(12) United States Patent
Lytle (10) Patent No.: US 11,160,890 B1
(45) Date of Patent: Nov. 2, 2021

(54) AUTOMATIC DISINFECTING WORKSTATION

(71) Applicant: Frank Lytle, The Villages, FL (US)

(72) Inventor: Frank Lytle, The Villages, FL (US)

( * ) Notice: Subject to any disclaimer, the term of this patent is extended or adjusted under 35 U.S.C. 154(b) by 0 days.

(21) Appl. No.: 17/216,176

(22) Filed: Mar. 29, 2021

Related U.S. Application Data (60) Provisional application No. 63/000,826, filed on Mar. 27, 2020.

(51) Int. Cl.
| | | |
|---|---|---|
| *A61L 2/10* | (2006.01) | |
| *A61L 2/24* | (2006.01) | |
| *A61L 9/20* | (2006.01) | |

(52) U.S. Cl.
CPC ........ *A61L 2/10* (2013.01); *A61L 2/24* (2013.01); *A61L 9/20* (2013.01); *A61L 2202/11* (2013.01); *A61L 2202/14* (2013.01); *A61L 2202/25* (2013.01); *A61L 2209/111* (2013.01); *A61L 2209/12* (2013.01)

(58) Field of Classification Search
None
See application file for complete search history.

(56) References Cited

U.S. PATENT DOCUMENTS

| | | | | |
|---|---|---|---|---|
| 9,637,916 B1 * | 5/2017 | Lytle | .............. | E04B 2/7405 |
| 9,856,643 B1 * | 1/2018 | Lytle | .............. | E04C 2/20 |
| 2008/0276630 A1 * | 11/2008 | Lukitobudi | .............. | B01D 5/0057 |
| | | | | 62/93 |
| 2010/0127189 A1 * | 5/2010 | Boyarsky | .............. | A61L 2/24 |
| | | | | 250/492.2 |
| 2017/0049915 A1 * | 2/2017 | Brais | .............. | A61L 2/10 |
| 2018/0064833 A1 * | 3/2018 | Childress | .............. | A61L 2/24 |

* cited by examiner

*Primary Examiner* — Andrew Smyth
(74) *Attorney, Agent, or Firm* — Invention To Patent Services; Alex Hobson (57) ABSTRACT

An automatic disinfection workstation system utilizes a disinfecting workstation-light to disinfect surfaces within the workstation and may also include an airflow disinfecting system that utilizes an airflow disinfecting light to disinfect an airflow through the workstation. The workstation may have three walls forming the workstation enclosure and the disinfecting workstation-light may be configured proximal to the top of the walls and emit ultraviolet light to deactivate or kill germs or viruses within the line of sight of the light. The disinfecting workstation-light is actuated over the workstation to produce light with various lines of sight to more effectively disinfect the workstation. In addition, a light-angle actuator may rotate the light to further increase the various lines-of-sight. This combination of traversing the light at various angles may further enhance the effectiveness of disinfecting the workstation. The airflow disinfecting light may be a separate light or may be the disinfecting workstation-light.

17 Claims, 5 Drawing Sheets

AUTOMATIC DISINFECTING WORKSTATION

CROSS REFERENCE TO RELATED APPLICATIONS

This application claims the benefit of priority to U.S. provisional patent application No. 63/000,826, filed on Mar. 27, 2020; the entirety of which is hereby incorporated by reference herein.

BACKGROUND OF THE INVENTION

Field of the Invention

The invention is directed to an automatic disinfection workstation system that utilizes a disinfecting light to disinfect surfaces within the workstation.

Background

People spend a lot of time in their workstations and they may very well carry germs, viruses and bacteria (pathogens) with them into the workstation. People may then touch surfaces in the workstation and then touch their eyes, nose or mouth that can lead to sickness and infection. Pathogens may also be air borne causing disease. There exists a need for a safe and effective means to disinfect a workstation.

SUMMARY OF THE INVENTION

The invention is directed to an automatic disinfection workstation system that utilizes a disinfecting workstation-light to disinfect surfaces within the workstation. The exemplary automatic disinfection workstation system may also include an airflow disinfecting system that utilizes an airflow disinfecting light to disinfect an airflow through the workstation. The workstation may have three walls and optionally a ceiling, forming the workstation enclosure and the disinfecting disinfecting workstation-light may be emitted onto these surfaces as well as surfaces including but not limited to, a desk or work surface and equipment, such a laptop, monitor, keyboard, chair, light, stationary, writing implements, phones and the like. The automatic disinfection workstation system may be configured to emit more light or spend more time disinfecting a primary work area of the workstation, such as a desk or work surface having a computer thereon than an occupant area of the workstation. The workstation may be divided when viewed from above into a work surface, such as a flat surface for computer work, for example, and an open area or occupant area. Emitted light may deactivate or kill germs or viruses within the line of sight of the light. The exemplary disinfection workstation system actuates the light over the workstation to produce varying lines of sight of the light and therefore, more effectively disinfect the workstation. In addition, the exemplary disinfection workstation system may incorporate a light-angle actuator that actuates the light and light angle, wherein the light is moved over the workstation at said light angle. This combination of traversing the light at various angles may further enhance the effectiveness of disinfecting the workstation.

The workstation surfaces and airflow may be disinfected using an ultraviolet germicidal irradiation (UVGI) method wherein short-wavelength ultraviolet (UV-C) light kills or inactivates microorganisms by destroying nucleic acids and disrupting their DNA. Exposure to this light makes these organisms unable to perform vital cellular functions and replicate. An exemplary ultraviolet light used in the present invention emits an ultraviolet light having a wavelength of 10 nm to 300 nm, and may be a middle ultraviolet light that emits an ultraviolet light having a wavelength of 200 nm to 300 nm or a far ultraviolet light that emits an ultraviolet light having a wavelength of 200 nm to 10 nm. A far ultraviolet light may be safer for human exposure and may be used while an occupant is in the workstation. Exemplary ultraviolet light may be emitted with a wavelength of substantially 222 nm, or 254 nm, wherein the wavelength is within about 2 nm of the listed wavelength and preferably within 1 nm of the listed wavelength. An ultraviolet wavelength of 254 nm disrupts the RNA of COVID-19 and the DNA of other viruses like the common cold & flu plus other pathogens.

The dose of ultraviolet radiation is important to ensure effective ultraviolet germicidal irradiation. The dosage, is a product of UV light intensity and exposure time and can be measured in microjoules per square centimeter, or equivalently as microwatt seconds per square centimeter ($\mu W \cdot s/cm^2$). To obtain a 90% kill for most bacteria and viruses the dose ranges from 2,000 to 8,000 $\mu W \cdot s/cm^2$. The automatic disinfection workstation system may provide a UV dosage of about 2,000 $\mu W \cdot s/cm^2$ or more, about 4,000 $\mu W \cdot s/cm^2$ or more. Also note that the automatic disinfection workstation system may utilize far UV that may be emitted while an occupant is in the workstation.

An actuator may be configured above the workstation and may move the disinfecting workstation-light over the workstation during a workstation disinfecting mode, such as from the opening to the back wall or connector wall, or across the workstation from a left side wall to a right side wall. The workstation light may be configured on a light support that extends over the walls of the workstation and the actuator may move this light support along actuator rails extending along the top or proximal to the top of the walls, such as along the left and right walls, or the connector wall and front opening. An actuator rail may extend over the opening of the workstation, or from the left wall to the right wall. The disinfecting workstation-light may be actuated over a substantial portion over the workstation or at least 50% or more of the length or width, or at least 75% of the length or width, or at least 90% of the length or width.

The disinfecting workstation light may also be actuated by a light-angle actuator that rotates the light a light angle from vertical. The light may be actuated by a first light angle and then be actuated over the workstation along the actuator rails and then be actuated or rotated to a second light angle and then again actuated along the actuator rails. This combination of movement at different light angles may provide effective disinfecting of the workstation including the work surfaces of the workstation. The light angle may be about 20 degrees or more, about 30 degrees or more, about 45 degrees or more, about 55 degrees or more and any range between and including the light angles provided. The automatic disinfection workstation system may move the disinfecting workstation light or sweep of the disinfecting workstation light in a particular area such as over the work surfaces having a computer or keyboard sitting on the surface to ensure effective disinfection of the all surfaces. For example, in a workstation disinfecting mode, the disinfecting workstation light light may be actuated along the rails and then stop over the primary work area and work surface having a computer and sweep back and forth over a sweep light angle to produce emitted light at a sweep range of angles. A sweep angle may be back and forth over a light angle, such as 30 degrees to one side of vertical and then back to 30 degrees on the other side of vertical. This may ensure a large range of incident light rays for effective disinfection. The disinfecting workstation light may produce a light that spreads over a limited area or may emit a light that fans out over a large area.

An exemplary automatic workstation disinfection system may further comprise an air disinfecting system that disinfects an airflow through the workstation. An air moving device may be configured to produce an airflow through the workstation, such as into or out of the workstation and an air disinfecting light may emit a disinfecting light onto the airflow to disinfect the airflow during an airflow disinfection mode. The actuator may rotate the workstation disinfecting light 180 degrees or upward to emit UV light onto the air flowing into or out of the work station. The air moving device may be configured over the wall of the workstation, such as in a ceiling or configured to produce an airflow through a conduit in the ceiling. An air disinfecting light may be configured in the conduit or proximal to the conduit to emit light as it flows through the conduit. In an exemplary embodiment, the air moving device produces an airflow into the workstation and the airflow in disinfected by the air disinfecting light to produce a clean flow of air down over the occupant and out of the workstation. A positive pressure may be produced by an airflow into the workstation and this positive pressure may produce an outward flow out through the opening to the workstation which may prevent untreated or non-disinfected air from entering.

An exemplary automatic workstation disinfection system may employ two separate disinfecting lights, the disinfecting workstation-light that is actuated over the workstation and the air disinfecting light configured to emit light onto an airflow through the workstation. However, a single disinfecting light may be used wherein the disinfecting workstation-light also emits light onto the airflow through the workstation. In an exemplary embodiment, the disinfecting workstation-light is actuated to a position wherein the emitted light is incident on the airflow through the workstation. The disinfecting workstation-light may be moved by the actuator along the rails to a suitable position and/or may be rotated by the light-angle actuator to emit light onto the airflow. For example, the disinfecting workstation-light may be actuated under the air moving device and then rotated by the light-angle actuator to emit light up into the airflow or into the conduit through which the airflow passes.

An exemplary automatic workstation disinfection system may comprise an occupancy sensor, such as a proximity, motion or line of sight sensor that detects when an occupant is in the workstation or when to enter or exit the workstation. An occupancy sensor may detect motion and may determine that no occupant is in the workstation if no motion is detected for a certain threshold time, such as 10 or more minutes, 20 or more minutes, 30 or more minutes and any range between and including the threshold times provided. An occupancy sensor may be configured proximal the opening of the workstation and may be coupled with a control system having a controller, such as a microprocessor or circuit to control the functions of the system. The control system may activate the workstation disinfecting mode when no occupants are detected in the workstation. The disinfecting workstation-light may be turned on and actuated during the workstation disinfecting mode. The control system may stop the workstation disinfecting mode when someone enters the workstation or motion is detected within the workstation. The airflow disinfecting mode may be initiated when an occupant is detected in the workstation. The airflow disinfecting mode may require the disinfecting workstation-light to be moved into position to disinfect the airflow into or out of the workstation. The disinfecting workstation-light may be rotated by the actuator 180 degrees or upward, for example. These functions may be operated automatically based on the occupancy determination of an occupant in the workstation and based on threshold times that may be programmed into the control system.

A primary work area of a workstation is an area where an occupant may spend most of their time, such as at a desk or a work surface for retaining a computer and work equipment. A primary work area may be a portion of the area of the workstation, such as about 50% or less of the cross sectional area or about 30% or less of the cross sectional area. The control system may be configured to move the disinfecting workstation-light to emit a larger dosage of light onto this primary work area, such as at least 1.25 more than the other areas, or at least 1.5 more, or even at least 2.0 more that the dosage of light received by the other areas.

An interior air disinfecting system may be configured to disinfect the interior air within the workstation and may utilize an air moving device to draw air from the interior of the workstation through a disinfecting apparatus, such as one or more filters and/or a disinfecting light, such as a UV light. In an exemplary embodiment, an interior air disinfecting apparatus includes an air filter followed by a disinfecting light, such as a UV light. This disinfecting light may be within an enclosure of the interior air disinfecting apparatus and therefore concerns about this light exposure on people may be avoided and UV light with a wavelength of 222 nm may be used. If the light is enclosed in the interior air disinfecting system, a wide range of UV wavelengths may be used, as the light is not emitted from the system, including UV light with wavelengths of substantially 222 nm and/or UV light with wavelengths of substantially 254 nm. An interior air disinfecting system may draw air through vents or openings in the work surface or may draw air directly into the apparatus through an inlet. One or more slits in the work surface may be coupled with a plenum to direct air drawn by the interior air disinfecting system into the air disinfecting apparatus. An exemplary interior air disinfecting system may disinfect the air within the workstation very quickly, such as every minute, or even as quickly as every 40 second or quicker. This rate is a function of the volume of air in the workstation divided by the air flow rate through the interior air disinfecting system. An exemplary automatic workstation disinfection system may employ one or more interior air disinfecting system which may be placed in strategic locations to circulate the air such that disinfected air is force, or blown from the units, toward an occupant. An interior air disinfecting system may be configured on a work surface and the outlet may exhaust disinfected air out toward an occupant sitting at a work surface, or an interior air disinfecting system may be configured under a work surface and may have a plenum coupled with apertures in the work surface to draw air in through the work surface and exhaust disinfected air out into the workstation, such as toward an entrance to the workstation. An interior air disinfecting system may also be configured or mounted on one or more of the walls of the work station or the ceiling of the work station. Finally, an exemplary interior air disinfecting system may be configured on the outside surface of a workstation and receive air from the interior of the workstation through an aperture in the workstation wall or ceiling.

In an exemplary embodiment, disinfecting air is forced into the workstation from the air disinfecting system configured above the wall or in the ceiling and interior air is pulled from the work surface into the interior air disinfecting system to produce a downward flow of disinfected air over an occupant therein. The outlet of the interior air disinfecting apparatus may be within the interior of the workstation or may expel the air out from the workstation, such as through an opening in a wall of the workstation.

The summary of the invention is provided as a general introduction to some of the embodiments of the invention, and is not intended to be limiting. Additional example embodiments including variations and alternative configurations of the invention are provided herein.

BRIEF DESCRIPTION OF SEVERAL VIEWS OF THE DRAWINGS

The accompanying drawings are included to provide a further understanding of the invention and are incorporated in and constitute a part of this specification, illustrate embodiments of the invention, and together with the description serve to explain the principles of the invention.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION OF THE ILLUSTRATED EMBODIMENTS

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

Figure 1:
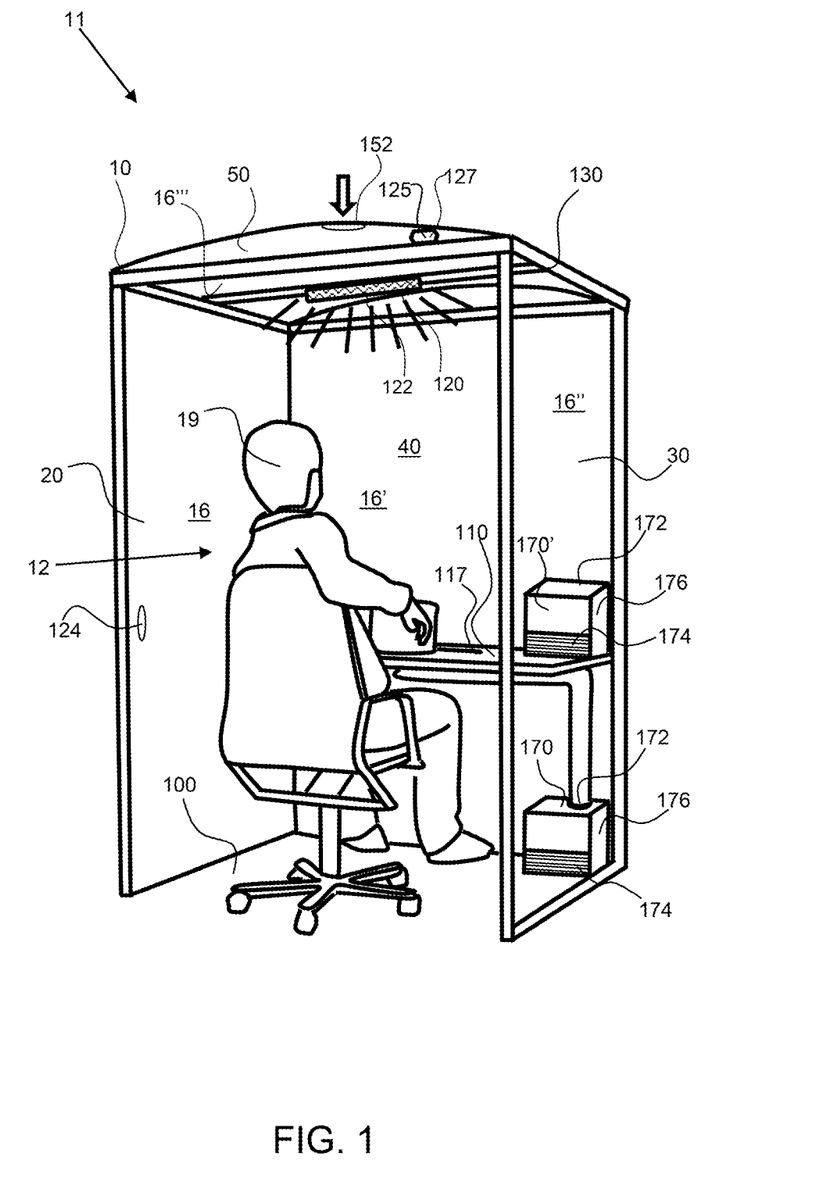
FIG. 1 shows an exemplary workstation having a workstation disinfecting system and an air disinfecting system that both utilize a disinfecting light to kill or deactivate viruses.

As shown in FIG. 1, an exemplary workstation disinfecting system 11 is configured to disinfect an exemplary workstation 10 having three enclosure panels 16 to 16", including a left wall 20, a right wall 30 and a back or connector wall 40. The workstation has an opening 12 for entry and a ceiling 50. A workstation surface disinfecting system 122 is configured with a work-station disinfecting light 120 that is moved by an actuator 130 over the work-station. The work-station disinfecting light may also be pivoted to change the line of sight of the light emitted and therefore more effectively disinfect the surfaces of the workstation. An exemplary air disinfecting system 152 moves air into or out of the work-station and utilizes an air disinfecting light to disinfect the air moving through the workstation. An occupancy sensor 124, such as a motion detector may be used to activate the workstation surface and/or air disinfecting systems. The air disinfecting system may be turned on when a person enters the workstation and the work-surface disinfecting system may be activated when a person leaves a workstation. A control system 125 having a controller 127, such as a microprocessor, may receive input from the occupancy sensor 124 and may initiate the actuator and/or the air moving device and disinfecting lights according to a programmed mode of operation.

As shown in FIG. 1 the occupant 19 is sitting in a chair in the occupant area 100 of the workstation 10 and an interior air disinfecting system 170 is configured to draw interior air through vents 117 in the work surface 110 into the interior air disinfecting apparatus 176. The interior air moves from the inlet 172 through the interior air disinfecting apparatus and is expelled from the outlet 174. The outlet is shown emitting the disinfected interior air into the workstation but may be configured to expel the disinfected interior air out of the workstation. A second interior air disinfecting system 170' is configured on the work surface and draws air in from above the work surface and expels disinfected air out over the work surface. An interior air disinfecting system 170 configured on a work surface may effectively capture bodily fluids a viruses expelled by an occupant sitting at a work surface, such as from coughs, exhaling sneezes and the like.

Figure 2:
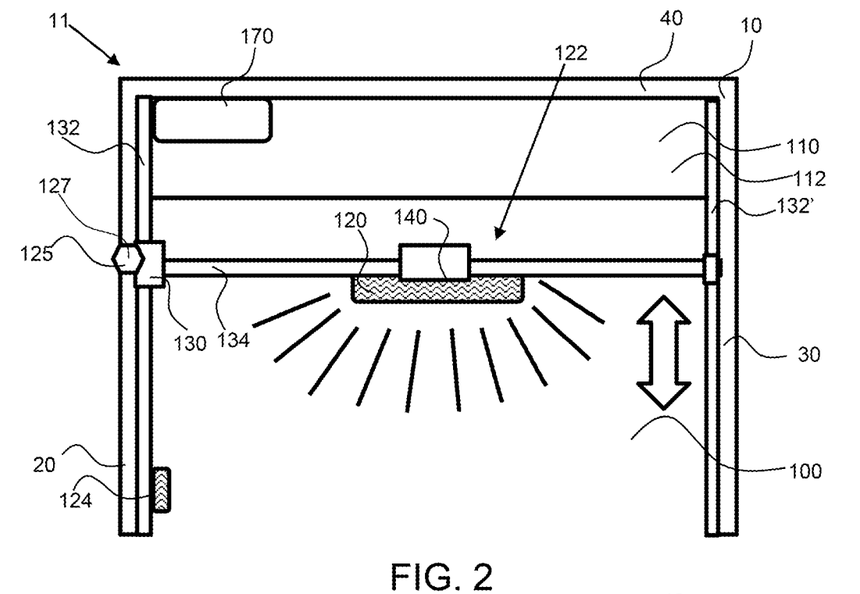
FIGS. 2 and 3 show a top view of an exemplary a workstation disinfecting system that moves a light back and forth over the workstation to disinfect work surfaces, wherein the light is moved back and forth over the workstation and is also rotated to change the line of sight of the light within the workstation.
Figure 3:
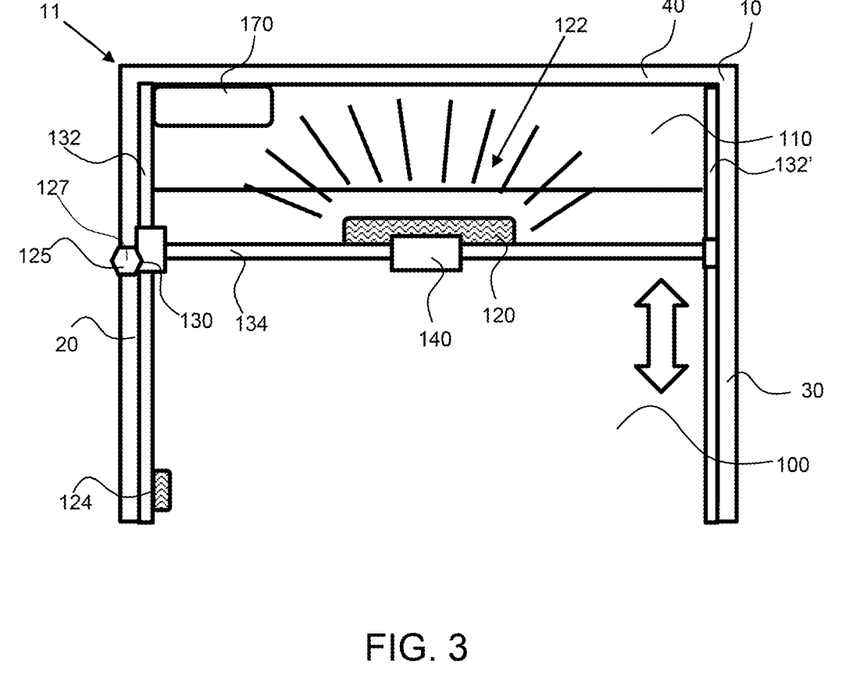
Figure 4:
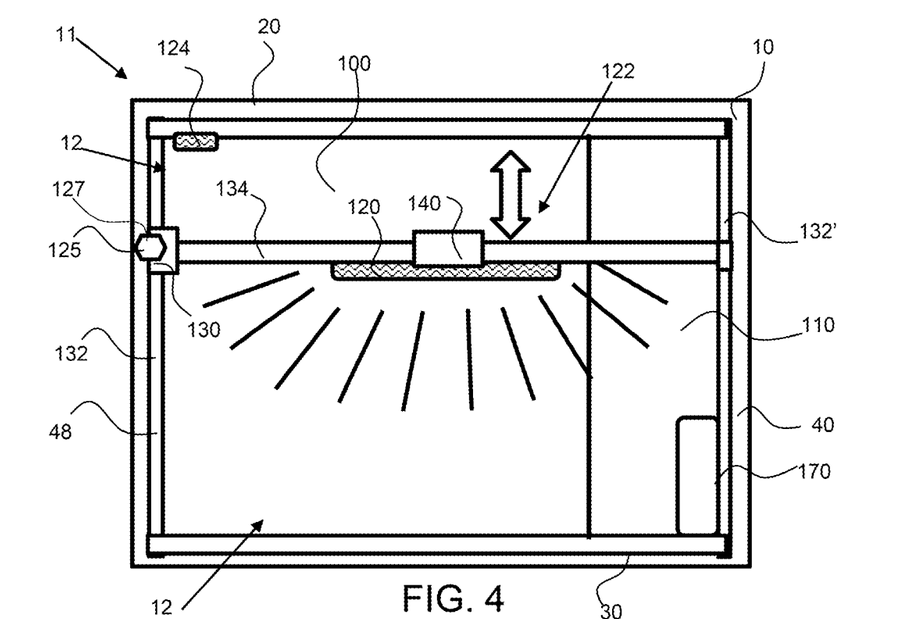
FIGS. 4 and 5 show a top view of an exemplary a workstation disinfecting system that moves a light back and forth over the workstation to disinfect work surfaces, wherein the light is moved back and forth over the workstation and is also rotated to change the line of sight of the light within the workstation.
Figure 5:
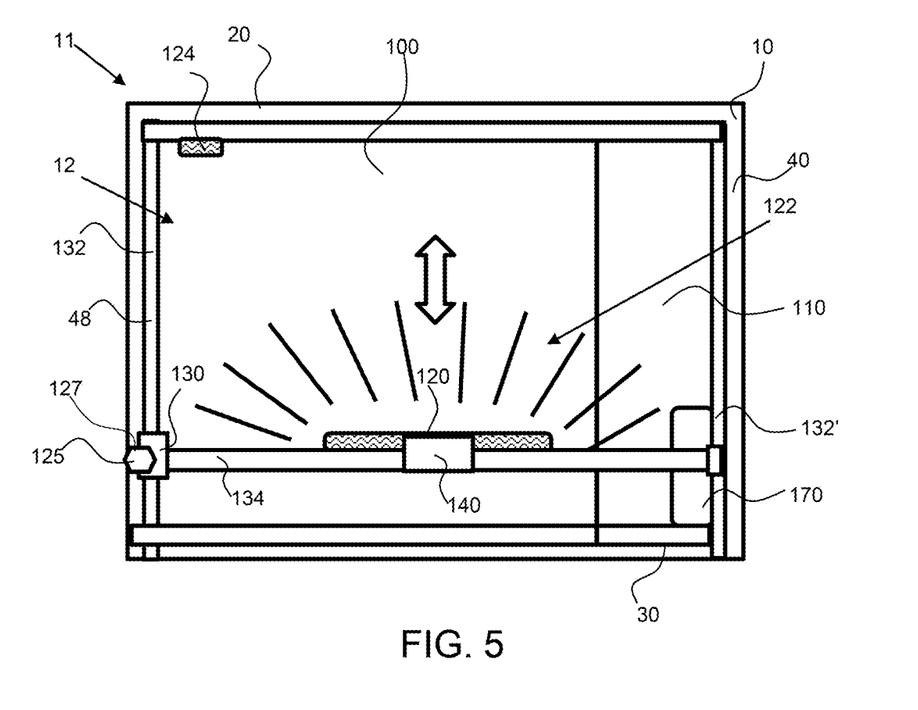

Referring now to FIGS. 2 to 5, an exemplary workstation 10 is configured with a workstation surface disinfecting system 122 that moves a disinfecting workstation-light 120 back and forth over the workstation to disinfect the workstation including the walls, ceiling and work surfaces 110, such as a desk computer, keyboard, walls and the like. As described herein, a primary work area 112, such as the work surface or desk may receive a higher dosage of disinfecting light than other areas of the workstation. The disinfecting workstation-light may be moved back and forth, by the actuator 130 and is may also be rotated by a light-angle actuator 140 to change the line of sight of the emitted light within the workstation. The actuator 130 may move the light support 134, such as a rod or beam, along the actuator rails 132, 132', configured on opposing sides of the workstation, such as on the left side wall 20 and right side wall 30, as shown in FIGS. 2 and 3, or along the back wall 40 and an opening rail 48 configured over the opening 12, as shown in FIGS. 4 and 5. The actuator 130 moves the light support and the disinfecting workstation-light over the workstation and the light-angle actuator 140 angles the light to provide more effective line-of-sight disinfecting.

As shown in FIG. 2, the light is angled a first light angle and in FIG. 3 the light is angled a second light angle, thereby producing a plurality of light emitted angles during the actuation of the light over the workstation. As described herein, the workstation surface disinfecting system 122 may stop the disinfecting workstation-light at a position and then rotate the light by the light-angle actuator to sweep the light over a sweep range of light angles. This may performed over the most used area of the workstation, such as over the desk portion or work surface 110 portion. Also, the light may be rotated during actuation over the workstation. Also, a workstation disinfecting system may be configured with rail in both configurations as shown in FIGS. 2 and 3 as well as shown in FIGS. 4 and 5. The system may employ two or more disinfecting workstation lights.

The workstation 10 comprises an occupancy sensor 124 that is configured proximal to the opening 12 to the workstation and may sense when the occupant(s) have left the workstation and may activate the workstation surface disinfecting system 122 and the disinfecting workstation-light 120 to turn on and the actuator to actuate the light. Again, a primary work area may received more disinfecting light exposure than other portions of the workstation. The disinfecting workstation-light may stop over this primary work area or may move more slowly over this area. The disinfecting workstation-light may also sweep over a ranges of light angles when configured over this primary work area.

As shown in FIGS. 2 and 5, an interior air disinfecting system 170 is configured on a work surface 110 to draw interior workstation air into an interior air disinfecting system. A second interior air disinfecting system (not shown) may be configured to draw air from vents 117 in the work surface. An exhaust flow from the outlet of an interior air disinfecting system may produce a flow of disinfected air toward an occupant or into the workstation. The occupant area 100 and work surface area 110 are shown as portions of the workstation 10 when viewed from above. The occupant area extends from the entrance to the work surface.

Figure 6:
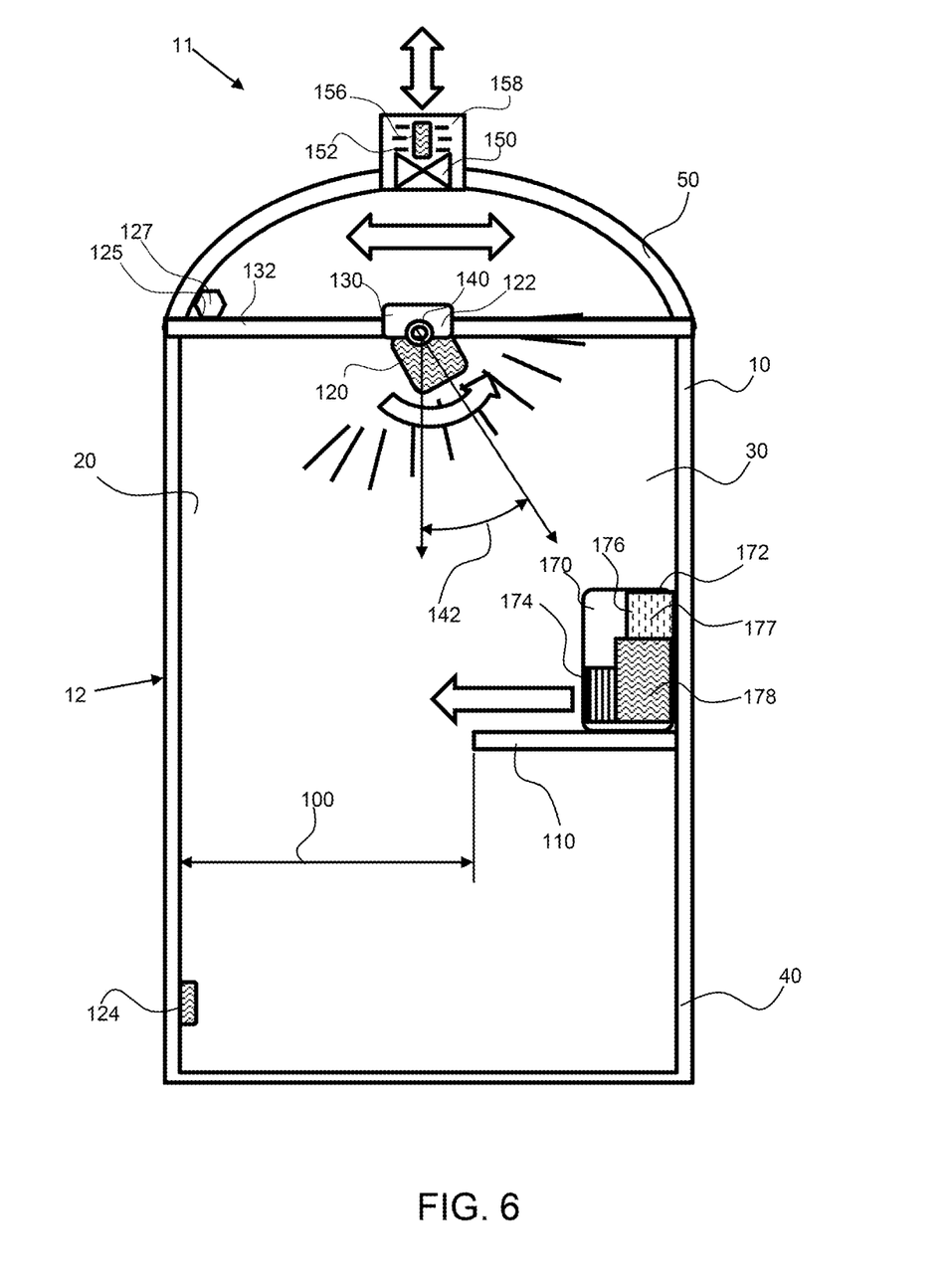
FIG. 6 shows a side view of a workstation having a workstation disinfecting system and an air disinfecting system that moves air into and/or out of the workstation and incorporates a disinfecting light to treat the air as it moves through the system.

As shown in FIG. 6, an exemplary workstation disinfecting system 11 has a workstation surface disinfecting system 122 and an air disinfecting system 152. The air disinfecting system utilizes an air moving device 150 that moves air through the workstation, such as into and/or out of the workstation, as indicated by the bold double sided arrow above the workstation, and incorporates an air disinfecting light 156 to treat the air as it moves through the system. The air moving device may produce an airflow through a conduit 158 in the ceiling 50 of the workstation, as shown, and the air disinfecting light 156 may emit light within or into this conduit. The light-angle actuator 140 is configured with the light and angles the disinfecting workstation-light a light angle 142 from vertical. The light angle is about 45 degrees fro vertical. A change in light angle may be at least 10 degrees, 20 degrees or more, 45 degrees or more, 90 degrees or more, 120 degrees or more, or as much as 180 degrees from a first to a second light angle. This workstation disinfecting system may be activated by the occupancy sensor 124 and the air disinfecting system 152 may be activated when an occupant is detected within the workstation 10.

Figure 7:
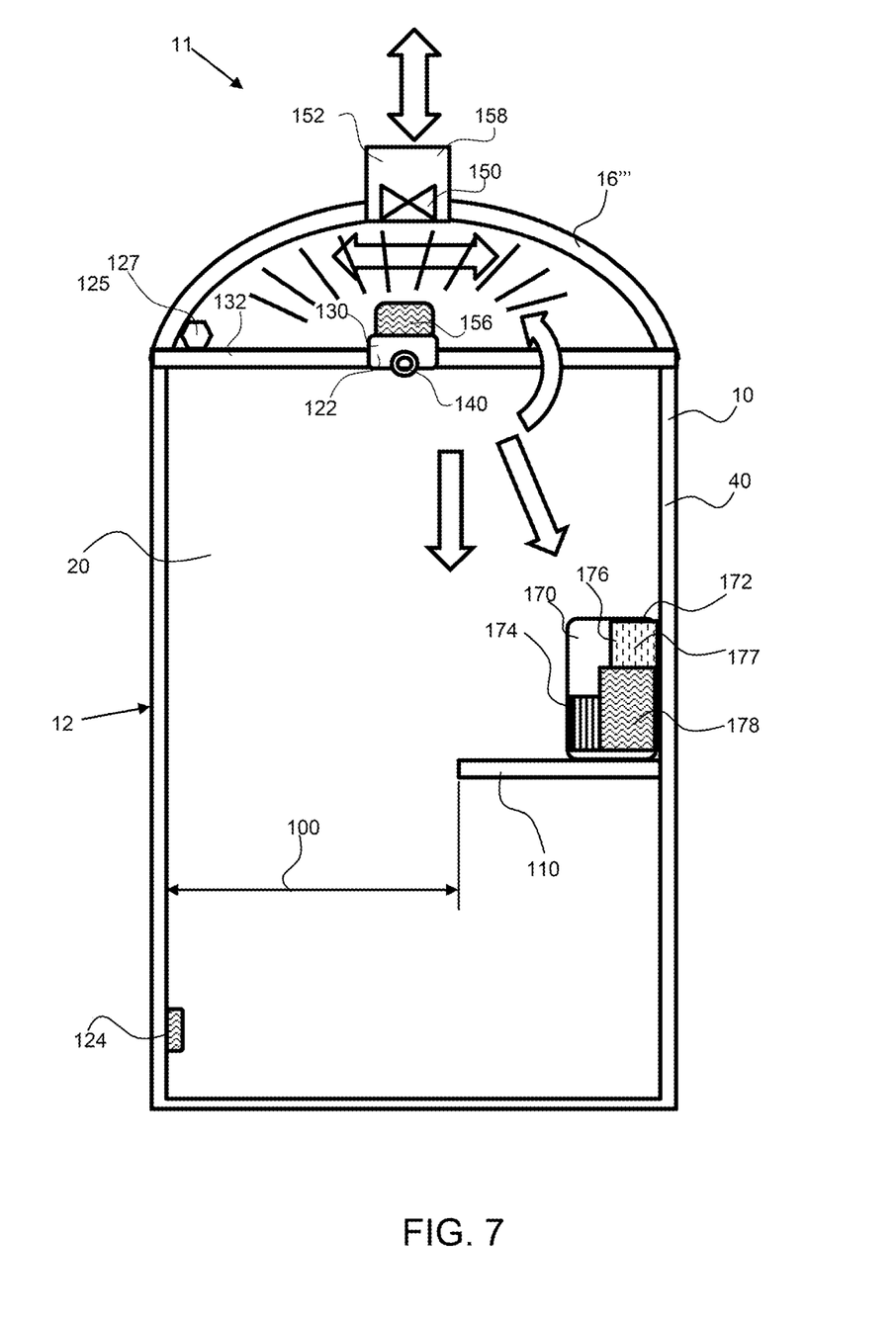
FIG. 7 shows a side view of a workstation having a workstation disinfecting system and an air disinfecting system that moves air into and/or out of the workstation and utilizes the disinfecting light of the workstation disinfecting system to treat the air as it moves through the system.

As shown in FIG. 7, an exemplary workstation disinfecting system 11 has a workstation disinfecting system 122 and an air disinfecting system 152. The air disinfecting system utilizes an air moving device 150, such as a fan or blower, that moves air into and/or out of the workstation, as indicated by the bold double sided arrow above the workstation, and utilizes the disinfecting workstation-light 130, coupled with the light-angle actuator 140 to disinfect the airflow as it moves through the workstation, such as through the airflow conduit 158. The disinfecting workstation-light is rotated by the light-angle actuator 140 to direct the light toward the air disinfecting system 152, whereby the disinfecting workstation-light 130 is also the air disinfecting light 156. As shown, the light is rotated upward or 180 degrees from a downward orientation that may be used for workstation disinfection. In this way, the airflow may be disinfected while the workstation is occupied and the workstation surfaces may be disinfected when the workstation is empty of occupants. This workstation disinfecting system may be activated by the occupancy sensor 124. This dual purpose system is effective and eliminates the need for a plurality of separate systems.

As shown in FIGS. 6 and 7, an interior air disinfecting system 170 has an inlet 172 and outlet 174. The inlet is drawing air through a plenum coupled with vents 117 in the work surface 110. The exemplary interior air disinfecting system has an air filter 177, such as a HEPA filter, having a particle capture efficiency of 99.97 or more to 0.3 micron particles, and a disinfecting light 178, such as a UV light. The flow of air when both the upper air disinfecting system and the interior air disinfecting system are utilized is depicted by the large bold arrows. The occupant area 100 and work surface area 110 are shown a portions of the workstation 10 along the depth of the workstation from the entrance to the back wall.

It will be apparent to those skilled in the art that various modifications, combinations and variations can be made in the present invention without departing from the scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. An automatic workstation disinfection system comprising:
   a) a workstation forming an enclosure having at least three walls;
   b) a workstation surface disinfecting system comprising:
   i) a disinfecting workstation-light that emits a disinfecting light;
   ii) an actuator that moves the disinfecting light over a workstation during a workstation disinfection mode;
   iii) a light-angle actuator that actuates the disinfecting workstation-light;
   wherein the disinfecting light is incident on workstation surfaces at a plurality of angles;
   iv) an air disinfecting system comprising:
   an air moving device that produces an airflow through the workstation:

wherein the disinfecting workstation-light is rotated to switch
the disinfecting workstation-light to an airflow disinfecting light that emits a disinfecting light toward the airflow during an airflow cleaning mode;
wherein the workstation comprises a ceiling;
wherein the air disinfecting system comprises a conduit extending through the ceiling; and
wherein the airflow is through said conduit extending through the ceiling; and wherein the air disinfecting light is actuated towards the conduit to be incident on airflow flowing through the conduit.

2. The automatic workstation disinfection system of claim 1, wherein the disinfecting workstation-light is moved over the workstation at a first light angle, and wherein the light-angle actuator actuates the disinfecting workstation-light to a second light angle and wherein the disinfecting workstation-light is moved over the workstation at said second light angle.

3. The automatic workstation disinfection system of claim 2, wherein the second light angle is at least 20 degrees different from said first light angle.

4. The automatic workstation disinfection system of claim 1, wherein the disinfecting workstation-light is an ultraviolet light that emits an ultraviolet light having a wavelength of 10 nm to 300 nm.

5. The automatic workstation disinfection system of claim 1, wherein the disinfecting workstation-light is a middle ultraviolet light that emits an ultraviolet light having a wavelength of 200 nm to 300 nm.

6. The automatic workstation disinfection system of claim 5, wherein the disinfecting workstation-light is has a wavelengths of about 254 nm.

7. The automatic workstation disinfection system of claim 1, wherein the disinfecting workstation-light is a far ultraviolet light that emits an ultraviolet light having a wavelength of 200 nm to 10 nm.

8. The automatic workstation disinfection system of claim 1, wherein the workstation further comprises a ceiling.

9. The automatic workstation disinfection system of claim 1, wherein the workstation comprises a primary work area comprising a work surface.

10. The automatic workstation disinfection system of claim 9, wherein the workstation comprises a work surface and a occupant area and wherein the workstation surface disinfecting system further comprising a control system that controls the movement of the disinfecting workstation-light to emit at least 1.5 times more disinfecting light onto the work surface than the occupant area.

11. The automatic workstation disinfection system of claim 1, wherein the workstation further comprises a ceiling and an air disinfecting system comprising:
 a) an air moving device that produces an airflow through the workstation;
 b) an air disinfecting light that emits a disinfecting light on the airflow to disinfect the airflow during an airflow disinfection mode.

12. The automatic workstation disinfection system of claim 1, wherein the air moving device is configured over the walls of the workstation and moves air into the workstation.

13. The automatic workstation disinfection system of claim 1, further including a second air disinfecting light that is configured in the conduit.

14. The automatic workstation disinfection system of claim 1, further comprising an occupancy sensor that detects if an occupant is in the workstation.

15. The automatic workstation disinfection system of claim 14, wherein the workstation disinfecting mode is automatically initiated when the occupancy sensor detects that there are no occupants in the workstation.

16. The automatic workstation disinfection system of claim 15, wherein the airflow disinfecting mode is automatically initiated when the occupancy sensor detects an occupant entering the workstation.

17. The automatic workstation disinfection system of claim 15, further comprising an interior air disinfecting system comprising:
 a) an air moving device having an inlet and an outlet and that draws interior air from an interior of the workstation into the interior air disinfecting system; and
 b) a disinfecting apparatus including an ultraviolet light that disinfects the interior air.

\* \* \* \* \*